United States Patent

Speitling et al.

[11] Patent Number: 5,993,456
[45] Date of Patent: Nov. 30, 1999

[54] DEVICE FOR MANUFACTURING A LATERAL BORE IN A TUBULAR BONE

[75] Inventors: Andreas W. Speitling, Kiel; Harm-Iven Jensen, Noer, both of Germany

[73] Assignee: Howmedica GmbH, Germany

[21] Appl. No.: 09/044,663

[22] Filed: Mar. 19, 1998

[30] Foreign Application Priority Data

Mar. 19, 1997 [DE] Germany .................. 197 11 441

[51] Int. Cl.⁶ ..................................... A61B 17/58
[52] U.S. Cl. ..................... 606/98; 606/64; 606/80
[58] Field of Search .................. 606/96, 98, 95, 606/80, 64, 65, 66, 67

[56] References Cited

U.S. PATENT DOCUMENTS

| | | | |
|---|---|---|---|
| 4,667,664 | 5/1987 | Taylor et al. | 606/97 |
| 4,781,181 | 11/1988 | Tanguy | 606/84 |
| 5,411,503 | 5/1995 | Hollstien et al. | 606/80 |

FOREIGN PATENT DOCUMENTS

| | | |
|---|---|---|
| 0 218 492 | 4/1987 | France . |
| 0 530 574 | 3/1993 | Germany . |
| 93 00 271 U | 3/1993 | Germany . |
| 93 17 847 U | 1/1994 | Germany . |
| 43 44 470 | 6/1995 | Germany . |
| 0 633 001 A1 | 1/1995 | United Kingdom . |

*Primary Examiner*—Michael Buiz
*Assistant Examiner*—Julian W. Woo
*Attorney, Agent, or Firm*—Lerner, David, Littenberg, Krumholz & Mentlik, LLP

[57] ABSTRACT

A method for manufacturing a lateral bore in a tubular bone for a bone nail to be guided through a transverse bore of a bone nail characterised by the following features;

knocking in the bone nail introducing an elongate transmitting unit for energy into the bone nail and aligning an effective end of the transmitting unit, directed transversely to the axis of the nail, to the transverse bore in the bone nail;

producing a hole which is relatively small in diameter by way of the effective end from the inside and drilling out the small hole from the outside, preferably to the core diameter of the bone screw.

9 Claims, 2 Drawing Sheets

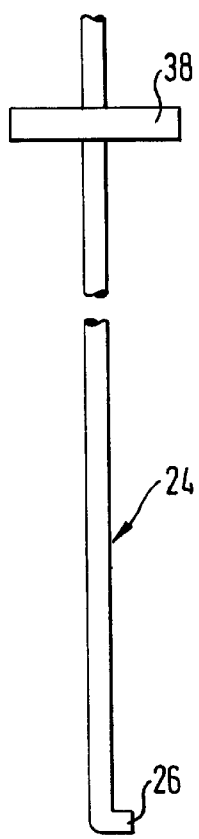
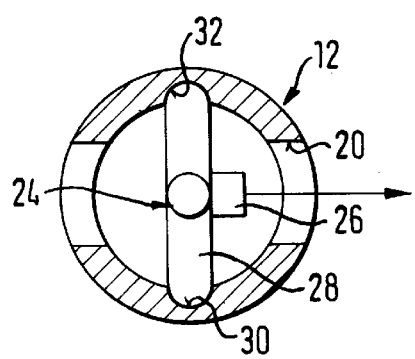
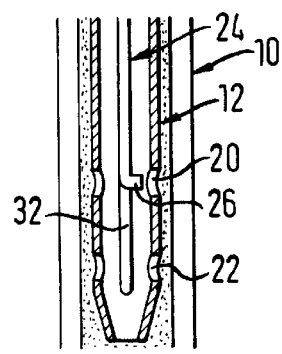
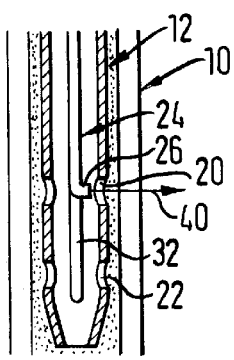
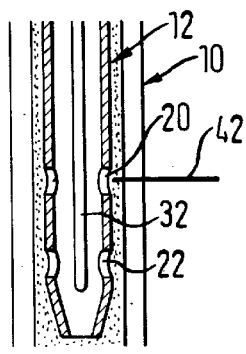
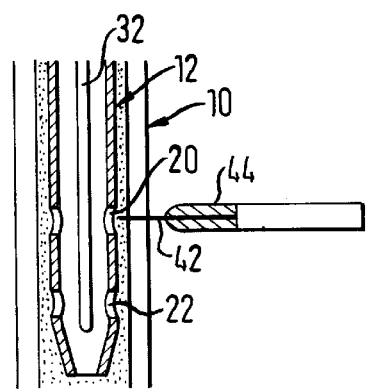

DEVICE FOR MANUFACTURING A LATERAL BORE IN A TUBULAR BONE

BACKGROUND OF THE INVENTION

The invention relates to a device for manufacturing a lateral bore in a tubular bone.

For the care of bone fractures in tubular bones it is known to apply so-called locking nails. These comprise transverse bores trough which bone screws may be guided in order to hold the bone fragments on the bone nail and to secure these against displacement and torsion. Before the bone screws can be screwed in, the holes must first be drilled into the substantia corticalis, this being at a relatively exact alignment to the transverse bore in the bone nail. This nail is usually hollow. On screwing in the bone screw not only must the first facing bore be met but also the opposite lying wall of the bone nail. A wrong alignment leads possibly to the nail screw only reaching through the allocated transverse bore onto the bone nail, then however abutting against the opposite lying wall of the bone nail. In this way a satisfactory screwing or anchoring of the bone nail is not ensured.

There are numerous methods and devices which have become known in order to locate the position at which a bore for the bone screw is to be placed. Most targetting devices function according to the principle of through illumination. The operator can, on a monitor, determine the position of the transverse bore in the bone nail within the bone and correspondingly place the drill mostly after a preceding incision with a suitable drill wire or likewise. However mechanical targetting apparatus have become known which can be placed onto the free end of the bone nail. The distance of the transverse bore from the end of the bone nail is known. Also the rotational position of the transverse bore may be indicated by a suitable marking at the end of the bone nail. With the help of a suitable targetting sleeve via the targetting apparatus the substantia corticalis can be drilled. The mechanical targetting apparatus is much less complicated than the above described method which furthermore has the disadvantage that one must operate with X-rays. The mechanical targetting apparatus on the other hand has the disadvantage that a correction of the determined position of the transverse bore is not possible. Indeed it may occur that the nail on knocking in distorts and its predetermined position no longer corresponds to the actual one.

BRIEF SUMMARY OF INVENTION

It is the object of the invention to provide a method for manufacturing a lateral bore hole in a tubular bone in which a complicated targetting method is avoided and a transverse bore call be produced precisely at the desired position.

With the method according to the invention the bone nail comprising the transverse bore is knocked into the hone tube as is usual up to now. Subsequently an elongate transmitting unit for energy is introduced into the bone nail, when the effective end of the transmitting unit is aligned to the transverse bore in the bone nail. With the effective end a relatively small hole from the inside is produced in the substantia corticalis and this hole is then subsequently drilled out from the outside in the usual manner preferably to the core diameter of the bone screw.

With the help of the method according to the invention the hole may be mechanically produced, with the help of water under pressure or also with the help of a high energy jet, for example of a laser beam.

The invention proceeds from the known fact that it is relatively easy to guide an elongate transmitting unit within a bone nail. The distance of the transverse bore to the free end of the bone nail is known as has been explained. It is merely required to so align the effective end of the transmitting unit in the rotational direction that it is aligned to the transverse bone. For this it is necessary that a guiding along the axis of the bone nail is effected in the manner that the effective end after reaching the predetermined introduction length in the bone nail is radially aligned to the transverse bore.

With the help of a mechanical tool, for example a rotating drill tip which can be driven in via an angular drive or a flexible shaft in the transmitting unit, in this manner a small hole may be produced in the substantia corticalis. Alternatively a hole may also be produced with water or fluid under pressure. In this case the transmitting unit contains a suitable conduit for fluid under pressure, which is connected to a corresponding nozzle at the effective end. At the other end the conduit is connected to a fluid pressure source. Finally the transmitting unit may comprise a guide for energy, in particular light energy, for example for a laser beam which is directed onto the substantia corticalis from the effective end in order to produce the desired bole, for example with a diameter of 0.5 mm.

The hole in the bone is aligned relatively exactly to the axis of the transverse bore so that from now on with the help of a usual drill the bore may be produced in the substantia corticalis. The drilling out is simplified according to one formation of the invention when a centering pin is introduced into the small hole and the drilling out is effected via the centering pin which is known per se.

The tool arrangement for carrying out the method requires an elongate transmitting unit with a deflection at the free end for aligning the effective end onto the transverse bore in the bone nail. The transmitting unit is in the position to transmit the energy of an energy source coupled to the transmitting unit to the effective end in order by way of the effect of energy in the substantia corticalis, to produce a small hole. So that the above mentioned radial alignment between the effective end and the transverse bore takes place, the bone nail comprises at least one guiding surface which cooperates with a guiding section of the transmitting unit. For this purpose the bone nail according to one formation of the invention may comprise diametrically opposite guiding grooves with which corresponding guiding sections of the transmitting unit cooperate.

In order to determine the introduction length, according to a further formation the invention on the transmitting unit there is provided a stop which comes to bear against the bone nail. If this is the case the operator knows that the effective end is aligned to the transverse bore in the bone nail. In a further formation of the invention the knocking in element or a suitable guiding instrument may be placed on the free end of the bone nail, for example by way of a tread connection. The transmitting unit is then introduced into the bone nail via a corresponding channel in the instrument and the length stop cooperates with the instrument.

The invention is hereinafter described in more detail by way of the drawings.

BRIEF DESCRIPTION OF THE DRAWINGS

FIG. 2 schematically shows the transmitting unit of the device according to FIG. 1.

FIG. 3 shows a section through the bone nail according to FIG. 1 along the line 3—3.

FIGS. 4 to 7 show the distal region of the bone nail according to FIG. 1 in various stages in the manufacture of a bore in the substantia corticalis.

DESCRIPTION OF THE PREFERRED EMBODIMENTS

Figure 1:
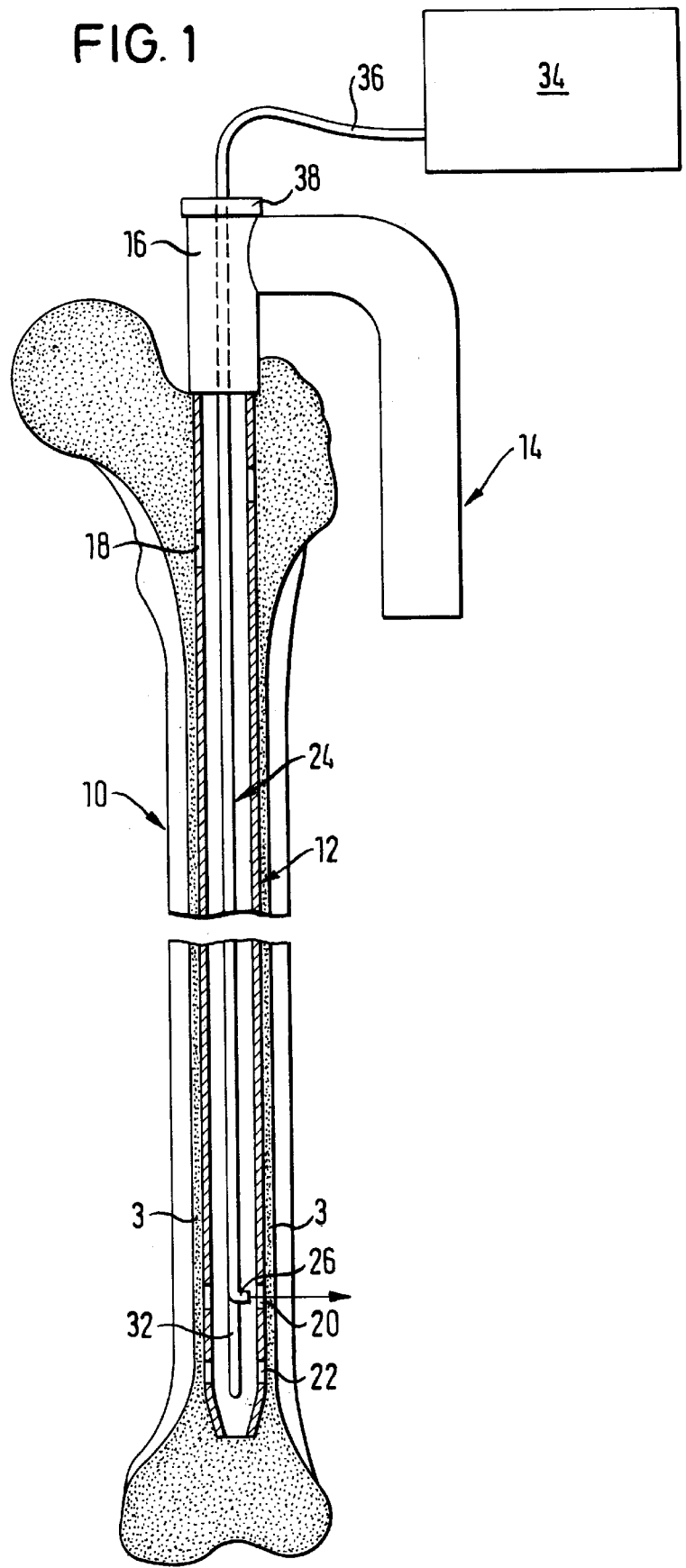
FIG. 1 schematically shows application of a device according to the invention on a femur.

In FIG. 1 there can be recognized a femur in whose intramedullary channel a locking bag nail 12 is driven. The locking nail 12 is driven in proximally with the help of a knocking-in instrument 14 which for example is connected to a section 16 via a thread connection to the nail 12. Such knocking-in instruments are principally known.

The hollow bone nail 12 in the proximal region is provided with an oblique through-bore 18 and in the distal region with two transverse bores 20, 22 (in reality each transverse bore 20, 22 is a pair of bores in the wall of the bone nail 12. For the sake of simplicity however it is always talked of only one bore).

Through the bores 18, 20 and 21 bone nails are introduced in order to "lock" the nail in the femur 10. For this purpose it is necessary to drill through the substantia corticalis in alignment to the transverse bores.

Into the locking nail 12 a transmitting unit 24 is introduced, here in the form of a conduit, which at the distal end comprises a right angled bent part 26. The conduit 24 which may be relatively rigid is held in a holder 28 (FIG. 3) which at the opposite end is rounded. The rounded ends engage into guiding grooves 30, 32 in the inner wall of the bone nail 12. The transmitting unit 24 or the conduit is fastened in the holder 28 this be⊐ also in the rotational direction. The fastening is such that the bent end 26 with its axis corresponds to the axis of the transverse bore 20, 22. It therefore depends of the depth of introduction of the transmitting unit 24 until when the axis of the bait part 26 coincides with the axis of for example the averse bone 20.

The bent part 26 is the effective end of a tool with whose help a hole is manufactured in the substantia corticalis of the femur 10. The effective end may thus be formed by a rotating mechanical tool, for example by a thin drill. The tool however may also consist of a nozzle which emits a thin jet of fluid under high pressure for producing the bole. It is further conceivable to provide a laser for the hole. The effective end is then formed corresponding to the end of a cleric which where appropriate is equipped with further optics.

The transmitting unit 24 thus serves for transmitting the energy for the tool at the effective end 26. It may thus contain a flexible shaft, a fiber-optic, a fluid conduit or likewise. Correspondingly the transmitting unit 24 according to FIG. 1 is connected to an energy source 34 to which at the same time there is allocated a suitable control device with tic help of which the intensity and duration of the energy to be applied at the effective end is determined.

In the present case the transmitting unit 24 is connected to a knocking-in instrument 14 which has a predetermined relation to the bone nail 12 as described. It is to be understood that instead of the driving-in instrument another instrument may also be applied as a bolder for the transmitting unit 24. The transmitting unit 24 extends through the section 16 of the instrument 14 and above the instrument 14 is connected to the energy source 34 via a conduit section 36. Further, to the transmitting unit there is connected a stop 38 which beam against the upper side of the instrument 14. The position of the stop 18 relative to the transmitting unit 24 can be adjusted. The stop 38 thus determines the introduction length of the transmitting unit in the bone nail 12. Since the distance of the transverse bows 20, 22 from the proximal end of the nail 12 is known, the axis of the effective end 26 of the transmitting unit 24 automatically reaches the height of the axis of the transverse bores 20 or 22 when the stop 38 bears on the instrument 14. Since in any case an alignment of the effective end 26 in the rotational direction takes place to the axis of the transverse bore via the guiding grooves 30, 32, the axis of the effective end 26 thus lies exactly on the axis of the transverse bore when the unit 24 is completely introduced and the stop 38 bears on the instrument 14.

The last described condition can be recognized in FIG. 4. In FIG. 5 it is shown how with the help of the tool of the effective end 26 a hole is produced in the substantia corticalis of the femur 10. The hole has for example a diameter of 0.5 mm. This procedure is indicated by the arrow 40.

In the treatment phase according to FIG. 6 the unit 24 is removed from the nail 12. A centering pin 42 is introduced into the hole according to FIG. 5 from the outside, as is shown in FIG. 6. With the help of the centering pin then from now on a bore is created with the help of a drill 44 which comprises a central bore so that it may be guided by the centering pin 42. Such drills are known per se. The hole which is manufactured with the help of the drill 44 has for example the core diameter of the bone scow which is subsequently screwed in and extends trough the transverse bore into the opposite substantia corticalis.

We claim:

1. A combination for manufacturing a lateral bore in a tubular bone for a bone fastener to be guided through a transverse bore of a bone nail, said combination comprising:

a bone nail having a longitudinal axis and having a circular cross-section formed by circular inner and outer surfaces defining a wall of generally constant thickness wherein said wall has two diametrically arranged guiding grooves formed therein extending parallel to said axis; and an elongate transmitting unit is provided which at a free end comprises a section bent to about 90°, with an effective end and whose other end is coupled to an energy source by which means the energy is transmitted via the transmitting unit into the effective end for producing a hole in the substantia corticalis and the transmitting unit having a guiding section coupled to the said guiding grooves and is guided by said grooves parallel to the axis in the bone nail.

2. An arrangement according to claim 1, wherein the transmitting unit comprises a stop for limiting the introduction length thereof into the bone nail.

3. An arrangement according to claim 2, wherein the stop is adjustable in the longitudinal direction of the transmitting unit.

4. An arrangement according to claim 2, wherein the stop cooperates with the guiding instrument.

5. An arrangement according to claim 1, wherein the transmitting unit transmits mechanical energy onto a rotating tool at the effective end.

6. An arrangement according to claim 1, wherein a guiding instrument which is connectable via threaded engagement to the facing end of the bone nail comprises a channel aligned to the axis of the bone nail for the guiding through of the transmitting unit over a predetermined distance.

7. An arrangement according to claim 1, wherein the effective end is designed and dimensioned such that the hole produced is relatively small if compared with the diameter of the bone nail.

8. A tool arrangement manufacturing a lateral bore in a tubular bone for a bone fastener to be guided through a transverse bore of a bone nail comprising an elongate transmitting unit having a conduit for fluid under pressure provided which at a free end comprises a section bent to about 90°, with an effective end and whose other end is coupled to a fluid pressure source, by which means fluid is transmitted via the transmitting unit onto the effective end for producing a hole in the substantia corticalis an the transmitting unit is coupled to a guide which is guided by a guiding surface parallel to the axis in a bone nail.

9. A tool arrangement for manufacturing a lateral bore in a tubular bone for a bone nail fastener to be guided through a transverse bore of a bone nail, comprising an elongate transmitting unit having a lead for light energy provided which at a free end comprises a section bent to about 90°, with an effective end and whose other end is coupled to a light energy source, by which means the light energy is transmitted via the transmitting unit onto the effective end for producing a hole in the substantia corticalis and the transmitting unit is coupled to a guide which is guided by a guiding surface parallel to the axis in a bone nail.

* * * * *

UNITED STATES PATENT AND TRADEMARK OFFICE
CERTIFICATE OF CORRECTION

PATENT NO. : 5,993,456
DATED : November 30, 1999
INVENTOR(S) : Speitling, et. al.

It is certified that error appears in the above-identified patent and that said Letters Patent is hereby corrected as shown below:

Column 1, line 9, "trough" should read -- through --.
Column 1, line 25, in between "through" and "illumination", insert -- - --.
Column 1, line 28, after "drill" insert -- , --.
Column 1, line 53, "hone" should read -- bone --.
Column 1, line 55, "when" should read -- wherein --.
Column 2, line 5, "bone" should read -- bore --.
Column 2, line 22, "bole" should read -- hole --.
Column 2, line 47, after "formation", insert -- of --.
Column 2, line 51, in between "knocking" and "in", insert -- - --.
Column 2, line 53, "tread" should read -- thread --.
Column 3, line 8, cancel the word "bag".
Column 3, line 30, "be ]" should read -- being --.
Column 3, line 34, "bait" should read -- bent --.
Column 3, line 35, "averse" should read -- transverse --.

UNITED STATES PATENT AND TRADEMARK OFFICE
CERTIFICATE OF CORRECTION

PATENT NO. : 5,993,456
DATED : November 30, 1999
INVENTOR(S) : Speitling, et. al.

It is certified that error appears in the above-identified patent and that said Letters Patent is hereby corrected as shown below:

Column 3, line 44, "cleric" should read -- fiber-optic --.
Column 3, line 52, "tic" should read -- the --.
Column 3, line 58, "bolder" should read -- holder --.
Column 3, line 63, "beam" should read -- bears --.
Column 4, line 1, "bows" should read -- bores --.
Column 4, line 7, "bore" should read -- bores --.
Column 4, line 24, "scow" should read -- screw --.
Column 4, line 25, "trough" should read -- through --.
Column 5, line 7, "an" should read -- and --.

Signed and Sealed this

Fourteenth Day of November, 2000

Q. TODD DICKINSON

*Attest:*

*Attesting Officer*       *Director of Patents and Trademarks*